United States Patent
Stillman

(10) Patent No.: US 6,248,390 B1
(45) Date of Patent: Jun. 19, 2001

(54) FIBER-WATER—WATER CONTAINING SOLUBLE FIBER

(76) Inventor: Suzanne Jaffe Stillman, 264 S. Linden Dr., Beverly Hills, CA (US) 90212

(*) Notice: Subject to any disclaimer, the term of this patent is extended or adjusted under 35 U.S.C. 154(b) by 0 days.

(21) Appl. No.: 09/510,400

(22) Filed: Feb. 22, 2000

(51) Int. Cl.$^7$ ................................. A23L 2/00; A23L 2/54
(52) U.S. Cl. ........................ 426/590; 426/74; 426/648; 514/40
(58) Field of Search ............................. 426/590, 73, 74, 426/648; 514/40

(56) References Cited

U.S. PATENT DOCUMENTS

| | | | |
|---|---|---|---|
| 4,283,432 | * | 8/1981 | Mitchell et al. ..................... 426/466 |
| 5,126,332 | * | 6/1992 | Ohta et al. ............................ 514/54 |
| 5,458,893 | * | 10/1995 | Smith .................................... 426/18 |

* cited by examiner

*Primary Examiner*—Nina Bhat
(74) *Attorney, Agent, or Firm*—Hogan & Hartson, LLP

(57) ABSTRACT

A shelf stable, ready to use, essentially tasteless and odorless water-like fluid for humans/animals comprised of safe water and a significant quantity of one or more water-soluble dietary fibers. Fiber-water is intended to be consumed by drinking or by enteral feeding alone, and/or in combination. The inventive liquid may be consumed directly hot or cold or after use, at any required temperature, in the preparation/reconstitution of beverages or liquid food product (e.g. coffee, tea, concentrates such as "HAWAIIAN PUNCH®", frozen concentrates such as lemonade/orange juice, soups and pet food). It can be used to enrich foods with soluble fiber through cooking, moistening, reconstituting or imbibing dried foods (e.g. oatmeal, rice, dried fruits, powdered soups, powdered beverages, powdered milks, nutritional shakes, "GATORADE®/TANG®/KOOL-AID®" products, gelatins, custards, puddings, and pet food). Fiber-water can be consumed in the frozen state either indirectly by adding it to a beverage as a cube or crushed "ice", or directly by licking a frozen "POPSICLE®" product). Fiber-water is safe water fiber enriched intending to be a replacement and/or adjunct to other water to ensure proper hydration while at the same time provide significant soluble fiber. Depending on the soluble fiber(s) used, and the user's individual metabolism, the invention is non-caloric or extremely low in calories. The soluble fiber(s) used are proven to moderate the postprandial rise in blood glucose (diabetes), address weight loss (obesity), lower serum cholesterol level (cardiovascular/heart), and address constipation and bowel regularity (colon cancer).

45 Claims, No Drawings

FIBER-WATER— WATER CONTAINING SOLUBLE FIBER

BACKGROUND OF THE INVENTION

1. Field of the Invention

The present application concerns generally components of the human diet and more specifically water and fiber.

2. Description of Related Art

Many of the major problems in human health revolve around which dietary components are truly essential for animal and human health and which components are merely hyped by various companies to sell product. A related problem is that of the accuracy of information regarding the appropriateness of a given food, nutrient or nutraceutical for a given individual. Certainly the "one size fits all" scenario is untrue when it comes to pharmaceuticals and nutrition. Further, the Federal Drug Administration has very little control over dietary supplements so that companies compete in making claims and launching new products, which may or may not be helping humans or animals that consume the products. New information constantly comes forth warning of serious potential interactions between nutritional supplements, ethical pharmaceuticals and various disease states. The present inventor is concerned with providing a composition that can be extremely beneficial to humans and animals with few, if any, dangers or drawbacks. In the following description consumption by humans should also be taken to include consumption by domestic animals—primarily dogs and cats. While many of the concepts discussed are applicable to other animals, the digestive systems of herbivores, particularly ruminates, varies tremendously from that of humans. Therefore, the thrust of the present invention is towards carnivores and omivores whose digestive systems more closely resemble those of humans.

One of the conundrums of human health is that dietary components, which may appear mundane, are actually incredibly essential. One such vital component that is frequently overlooked or given insufficient importance is water. Although water is not metabolized, it is absolutely essential for metabolism. A majority of the weight of the body is water which serves as the solvent for the chemical reactions of life. Water is the largest component of many living cells, and various nutrients needed for cellular growth and survival enter the cells dissolved in water. After metabolism, the waste products are carried away by water. If water intake is grossly neglected death can occur in as little as three to five days.

It is generally agreed that the average adult person should consume at least eight, 8 oz. glasses of water per day—more if the individual is undergoing stress that leads to increased loss of water. Unfortunately, most people drink water only when they feel parched. Generally, individuals do not consume sufficient water to completely address and/or reverse dehydration. Once dehydration begins the thirst response becomes even less effective as one ages. Older people are less likely to drink sufficient water and, hence, are more likely to suffer from dehydration. The reader's attention is drawn to "Problem: thirst, drinking behavior, and involuntary dehydration" by Dr. John E. Greenleaf, of NASA, (Medicine and Science in Sports and Exercise, 24:645 (1992)).

When the body is dehydrated, nutrients cannot be as readily delivered to the cells nor can waste products be as readily removed. With dehydration viscosity of the blood is increased so that efficiency of circulation is decreased. Such impaired circulation can ultimately lead to vascular damage and disease. At the same time, because the dehydrated body seeks to reverse this situation, more water is removed from the bowel. This causes excessive compaction and hardness of digestive residues with resulting constipation and potential accumulations of toxins in the bowel (which toxins may ultimately be absorbed into the blood stream). Further, there is abundant evidence that constipation may lead to a myriad of medical problems related to the gastrointestinal track including colon cancer, possibly as a result of prolonged contact between cells of the colon and toxin laden feces.

Because of the dehydrated situation of the body, filtration of wastes by the kidneys is reduced resulting in an even more significant buildup of toxic or waste products in the circulation. These wastes can exacerbate vascular damage while the high osmotic level of the blood and the high level of waste products can actually result in kidney damage. Of course, damaged kidneys are even less able to remove wastes and toxins. This results in a "chain reaction" where even more toxins and wastes accumulate and the overall damage becomes greater and greater.

Adequate intake of safe water can address the basic problems of dehydration. "Safe water" means water that meets the safety standards for drinking water promulgated by the federal and state governments in the United States. In other countries appropriate governmental entities set the standards for "safe water." However, even with an adequate intake of water, constipation due to low fiber intake and the damage it engenders continues to be a significant problem. This is due, in a large part, to the life style and diet of our industrialized society.

Unquestionably as a society, we are suffering from a deplorable lack of dietary fiber. We are constantly warned by the medical profession and other experts that this lack of fiber can, and does, kill. Our diets are replete with "empty" calories—refined foods loaded with fats and sugars—and contain few whole foods. When it comes to fiber many believe that a daily bowl of cereal is adequate. Our supermarkets and pantries are stuffed with brightly packaged, overly refined, prepared foods that are usually fiber-free or very low in fiber. The presence or absence of dietary fiber greatly influences one's ability to expel solid wastes. It has been estimated that about one in 19 individuals in our society has a health condition that requires special attention. In many cases this makes the need for adequate fiber and water, even more important to these individuals. Due to modern medicine's success in combating contagious disease, and with a better understanding of aging and our ability to medically address the aging process, we are living longer. But can we live healthier?

Fiber or "roughage" is a component of food that remains undigested as it passes through the gastrointestinal system. The vast majority of dietary fiber consists of polysaccharides of plant origin. The most obvious fiber is the cellulosic wall that surrounds plant cells. Many of these cells are actually called "fibers", hence the name "fiber" for this dietary component. However, there are actually two forms of fiber: insoluble fiber—the classic cellulosic material, and soluble fiber—water soluble polysaccharides that are not digested by human or carnivore digestive systems. Both types of fiber bind considerable water and, thus, have a softening effect on the stool. However, soluble fiber may, depending on the precise polysaccharides involved, be metabolized or partially metabolized directly by bacteria in the colon. Both type of fibers tend to increase motility within the gastrointestinal tract thus speeding transit time of wastes and lowering the risk of acute and chronic medical problems. Like water fiber is essential for human health and is not metabolized by humans.

It has been discovered that dietary fiber appears to moderate the rate at which sugars and fats are absorbed from the intestine. The exact reason for this effect is not completely understood. In the case of simple sugars, slowed absorption translates to a more gradual rise in blood sugar following eating. This is important in the managing of diabetes and may also help prevent adult onset diabetes. In the case of fats, the fiber seems to help prevent damaging levels of cholesterol in the blood. This seems to be due to a binding of bile salts and cholesterol to the fiber so that these materials are excreted with the feces rather than being absorbed or reabsorbed. Studies show adequate fiber clearly lowers the risk of heart disease and tends to bind toxins, including toxic metals, allowing them to exit safely from the digestive system.

In fact, it has been suggested that deficiency in dietary fiber is related to numerous disease states, including colon cancer, heart disease, cerebral apoplexy, appendicitis, and diabetes. This is apart from those diseases more closely linked to constipation, such as intestinal toxemia, hemorrhoids, irritable bowel syndrome (EBS), colitis, diverticulitis, varicocele, and cholelithiasis (gall stones). It is believed that dietary fiber performs various useful physiological functions including reduction of serum cholesterol, limitation of insulin secretion, and acceleration of bowel evacuation. All these factors make fiber a very important nutrient substance, the sixth most important by some commentators, although it is not actually metabolized.

Any water-soluble carbohydrate polymer can act as dietary fiber as long as no human enzymes are capable of hydrolyzing these polysaccharides into simple sugars. Preferentially, the polymers should also not be readily metabolized by bacteria common in the human gut so they can continue to provide a "bulking" effect. However, some types of soluble fiber are metabolized by and do promote growth of beneficial bacteria. This generally has a positive effect as the beneficial bacterial may also tend to lubricate the stool and/or prevent the growth of other bacteria that may release toxins (Leon Prosky, J. of AOAC Int'l. 82:223–35(1999)).

Soluble fiber comes from a wide range of plant sources. Water-soluble plant pectins and pectic materials, galactomannans, arabanogalactans and water-soluble hemicelulose can act as soluble fiber. Many plant "mucilages," gums, and soluble polysaccharides found in grains, seeds, or stems such as psyllium, guar, oat (beta glucans), astragalus (gum traganth), gum ghatti, gum karaya (Sterculia gum), and gum acacia are also soluble fiber. Algal polysaccharides such as agar or carrageenan also behave as soluble fiber as do other indigestible carbohydrates, such as maltodextrins or dextrins, produced by chemical or enzymatic digestion (e.g., partial hydrolysis) of starch, gums and other carbohydrate polymers. Soluble cellulosic ethers and other derivatives such as carboxymethyl cellulose behave as soluble fiber as do indigestible carbohydrate polymers artificially prepared using bacterial enzymes. Non-digestible storage carbohydrates such as inulin are also important soluble fibers. A number of companies are now providing an entire range of "soluble fiber" materials. For example, TIC Gums of Belcamp, Md., Novartis Nutrition of Minneapolis, Minn. and Imperial Sensus of Sugar Land, Tex. provide soluble fiber compounds of food grade.

Soluble "fiber" is known to provide a novel opportunity for improving the characteristics of fiber-poor refined foods. Fiber was removed from food products because in many cases it made the foods coarse, unpalatable or difficult to process. Adding insoluble bran or other similar fiber to foods may provide more roughage but can also degrade the favorable properties of the foods. For example, cakes or pastries made from flours high in insoluble fiber may have inferior taste and texture. Excess insoluble fiber may upset the digestion and lead to a number of digestive problems. On the other hand, soluble fiber is generally well tolerated, often improves the texture or other physical characteristics of the food product and is generally innocuous. Consequently, there are a growing number of food products, ranging from baked goods to "shake-like" beverages, contain added fiber in the form of soluble fiber. Soluble fiber can restore the benefits of fiber to our highly refined diet.

There are a number of "medical" or laxative products on the market that are based on soluble fiber. Various different brands are based on psyllium seed carbohydrates or on soluble cellulose derivatives (e.g., carboxymethyl cellulose). These products are replete with sugar, colors, dyes, artificial flavors, and artificial sweeteners. Generally, they do not comfortably fit into a "normal" diet. Usually they are powders that must be mixed with water to make a more or less thick, murky, slimy or even gritty solution. Further, their directions are rife with warning such as "TAKING THIS PRODUCT WITHOUT ADEQUATE FLUID MAY CAUSE IT TO SWELL AND BLOCK YOUR THROAT OR ESOPHAGUS AND MAY CAUSE CHOKING. DO NOT TAKE THIS PRODUCT IF YOU HAVE DIFFICULTY IN SWALLOWING, IF YOU EXPERIENCE CHEST PAIN, VOMITING, OR DIFFICULTY IN SWALLOWING OR BREATHING AFTER TAKING THIS PRODUCT SEEK IMMEDIATE MEDICAL ATTENTION."

Despite the tremendous benefits of soluble fibers, such a warning points out that dry packaged soluble fiber products are not the safest way to obtain soluble fiber. Fluid ingestion is an important, even vital, part of consuming soluble fiber. Further such a warning makes it clear that a safe and effective means for administration of soluble fiber is still needed because many consumers routinely disregard label directions and warnings.

SUMMARY OF THE INVENTION

It is an object of the present invention to simultaneously provide both essential water and essential dietary fiber.

It is another object to safely provide an optimal combination of water and fiber—two essential elements of human health.

It is a further object of the present invention to provide soluble dietary fiber in a form that guarantees that adequate water accompanies the fiber to render it optimally functional.

It is another object of the present invention to provide fiber and safe water in a simple, and pleasant to ingest convenient format.

The present invention discloses a water-like fluid that contains safe water and a significant quantity of soluble dietary fiber. The resulting solution, fiber-water is generally optically clear and has physical properties similar to potable water. Fiber-water can be used as a replacement for -bottled or tap water as a means to ensure proper hydration. Depending on the soluble fiber used, fiber-water is either non-caloric or extremely low in calories. The amount of soluble fiber is adjusted so that consumption of an adequate amount of fluid to ensure hydration (e.g., eight, (8), 8 oz. glasses per day) will also provide an optimal amount of dietary fiber. This is particularly valuable in stressed situations where the diet may not provide adequate fiber without supplementation. The constant metered supply of fiber provided throughout the day may be preferable to the "bolus" administration of fiber. Too much fiber at one time can, in fact, actually have a detrimental effect on some gastrointestinal conditions. Additionally, the constant presence of soluble fiber in the digestive tract provides the known beneficial effects of moderating the postprandial increase in blood glucose, modulating serum lipid levels, and suppressing appetite.

The present invention, fiber-water, is prepared by dissolving any of a number of water-soluble polysaccharides in safe potable water. Either purified water or natural water (e.g., mineral water) can be used. However, because hydration is a major object of the invention, the base water should be relatively low in dissolved salts (aka dissolved solids). Preferably the base water will not contain more than about 500 mg./1 dissolved salts. This invention is intended to include any soluble fibers; however, at this time the most preferred soluble fibers are derived from polysaccharides. Especially preferred polysaccharides are refined dextrins or maltodextrins produced by hydrolysis of starch (e.g., corn or potato starch), purified inulins (fructo-oligosaccharides) produced from plants such as dahlia or chicory, and partially hydrolyzed or otherwise fractionated vegetable gums such as partially hydrolyzed guar gum. A single type or mixture of more than one soluble fiber can be used to formulate fiber-water.

One way of using the invention is to provide the proper daily requirement of fiber spread over the eight, (8), 8 oz. glasses of water recommended to insure proper hydration. The invention is also useful to provide fiber and water in enteral feeding situations and to provide fiber to children and infants. In some applications color may be added as an indicator of the amount of fiber present because different strengths of the fiber solution are contemplated. In other situations color can be added to provide a more desirable appearance. The material can be consumed directly or can be used in any food to which water must be added. It is also contemplated that the invention can be used to ensure hydration and regularity of domestic animals—primarily cats and dogs. However, any carnivore or omnivore should benefit from the invention. Herbivores have very different gut bacteria and may be able to metabolize the soluble fiber. Therefore, these animals must be tested on a case by case basis.

DETAILED DESCRIPTION OF THE PREFERRED EMBODIMENTS

The following description is provided to enable any person skilled in the art to make and use the invention and sets forth the best modes contemplated by the inventor of carrying out her invention. Various modifications, however, will remain readily apparent to those skilled in the art, since the general principles of the present invention have been defined herein specifically to provide a water-like drink containing significant amounts of soluble fiber.

The current trend in foods is to add fiber and soluble fiber to a variety of food products. There are, however, potential drawbacks to this trend. To be fully effective soluble fiber must be combined with an adequate intake of water—certainly not available in dry goods and baked goods. This is true for both soluble and insoluble fiber. Although the "shake-like" and other soluble fiber beverages or mixes to which water must be added do contribute water, they, like most dry goods, also contribute a significant source of calories to the diet—a major problem with today's diets and something clearly not needed by our generally overfed population. While it is possible to limit the caloric content of the fiber-containing beverages through the use of non-nutritive sweeteners, this amounts to adding chemicals that may create or exacerbate health problems. Therefore, the present inventor has developed a superior solution based on the unique synergistic interaction between water and soluble fiber.

In experimenting with various types of soluble fiber, the inventor noticed that a number of the more refined materials, such as lower molecular weight grades of inulin (for example see U.S. Pat. No. 5,968,365), specialized dextrins, maltodextrins and partially hydrolyzed guar gums can actually produce a clear, or virtually clear, and virtually colorless solution in water. Further, these soluble fibers are essentially tasteless at the preferred concentrations for consumption and essentially non-metabolized by the human digestive tract.[2] Thus is produced an entire new class of beverage-namely, "fiber-water." Dissolving appropriate water-soluble fiber to a concentration of generally 0.1–10% (by weight) produces fiber-water. The resulting product is essentially water-like. Any of the soluble fiber materials listed above can used individually or combined so long as the resulting product has the desired "water-like" characteristics—namely little or no taste, water-like viscosity, and few or no calories. Some of the carbohydrate polymers may contain small amounts of material that is absorbed and does contribute calories to human metabolism. However, the number of calories is small compared to the significant dietary fiber contributed and can be minimized by careful selection and blending of different soluble fiber materials. Furthermore, there are individuals and or species that are unable to absorb any of the soluble fiber and so that no calories are added.

[2] Many of these materials contain a small component of metabolizable carbohydrate. For example, inulins often contain about 1.6 food calories (kilocalories) per gram. This is a tiny fraction of the calories provided by a fully metabolizable carbohydrate. In many cases the exact amount of carbohydrate absorbed, if any, varies from person to person depending on age, weight, health condition, etc. The exact number of calories absorbed can be discovered only by careful metabolic analysis. However, the maximum number of absorbed calories will not exceed the maximum given for a specific fiber type (e.g., 1.6 food calories per gram for a specific inulin).

Fiber-water is the perfect addition to the modem human diet as well as that of appropriate animals. It adds few, if any, calories and is readily substituted for bottled water as a safe source of hydration. In the intestines, water is withdrawn from the intestinal contents, and as the effective concentration of soluble fiber increases, the viscosity-increasing and sequestering properties of the soluble fiber result in slowed absorption of sugars and altered absorption of fats. This is of major significance in diabetes, heart disease, and equally significant additional health conditions. Ultimately in the colon the hydrophilic properties of the soluble fiber have a softening and bulking effect on the stool. Thus, fiber-water is a unique, consistent, safe, easy to use single product that simultaneously ameliorates the problems of dehydration and constipation. Further, there are indications that the viscosity enhancing and carbohydrate absorption-slowing properties of the soluble fiber result in appetite suppression both by creating a feeling of fullness and by moderating swings in blood sugar. Scientific as well as popular literature is filled with positive effects of fiber on weight control both in humans and domestic animals. Thus, fiber-water is not only non-caloric or very low in calories but has additional positive effects on weight control.

Although the inventor contemplates fiber-water as a direct way to add water and fiber to the diet, it is also a feature of the invention that it can also be used to add fiber to other foods. For example, any packaged food or beverage can be reconstituted with fiber-water to yield a fiber-enhanced food and/or beverage. Because fiber-water is based on safe water, it results in a safe food product even if the product is not heated to destroy microbes, although soluble fiber polysaccharides are generally stable during the cooking process. This means that if fiber-water is used to cook foods, such as grains (rice), oatmeal, and legumes, that imbibe water during the cooking process, these foods will also become fiber enhanced. Further, if dried or concentrated fruits, vegetables, etc. are soaked in fiber-water, they will become fiber-enriched as well as softened and more digestible due to the absorption of water. Fiber can readily be added to all types of packaged food including gelatin products and to canned concentrated foods such as soups. Further, since fiber-water is heat stable it can be used to prepare fiber enriched hot beverages. In addition, fiber-water can be frozen to provide fiber-water-based ice cubes, crushed ice, pops, etc.

An important aspect of fiber-water is that it preferably has a "water-like" appearance. By this the inventor means that the solution is essentially clear. People tend to relate clear solutions to purity. Some soluble fiber materials yield a cloudy or murky solution. It is preferred that fiber-water utilize materials that yield essentially clear solutions. As already mentioned, several available non-digestible carbohydrates produce "water clear" solutions. Generally partial hydrolysis or fractionation of the soluble fiber materials already discussed (e.g. partially hydrolyzed guar gum) will lead to clearer solutions. To date many manufacturers of soluble fibers have been concerned with using their products in solid foods where texture of the ingredient is most important. Therefore, there has been little effort in producing materials that make clear solutions. Additionally; there has been no effort to combine "water clear" soluble fiber with safe water to create fiber-water.

Besides universal use as a hydrating and fiber providing material, fiber-water is especially useful in situations of stress. It is believed that stress, both physiologically and psychologically wrecks havoc on the body and alters or effects bowel regularity as well as other bodily functions. When under stress humans and animals are known to reduce their consumption of water. Yet when the body is stressed by disease, additional water is required, yet this is exactly when many reduce their fluid intake. Further stress may influence people to prefer sugar-laden beverages (comfort food) or caffeine beverages for alertness—these types of beverages actually increase ones water requirement and may lead to dehydration. Thus, it is beneficial to provide fiber-water as opposed to plain water in emergency supplies to be used in case of natural disaster—fire, flood, storm, earthquake, or hurricane and it is suggested fiber-water be stocked by FEMA or its international counterparts. During such a disaster people are stressed and are often forced to move from their homes and everyday surroundings. Emergency situations often dictate a shortage of food and water and/or that food and water will be available at abnormal times. This combined with the general shortage of fresh fruits and vegetables, which are a key source of dietary fiber, during such an emergency naturally leads to loss of regularity. Emergency food drops rarely contain fresh fruits and vegetables. Having to deal with the emergency is bad enough. Adding severe constipation and dehydration simply makes a bad situation worse. Assuring ample supplies of fiber-water is intended to alleviate many of these problems.

Natural catastrophes and emergencies are certainly a source of stress as are medical problems. Numerous and varied medical conditions, both short term and long term, may require feeding an individual through a tube. The two types of tubes used most commonly are the naso-gastric tube and the gastrostomy tube. In either case nutriment is supplied directly into the stomach. The present inventor is a named inventor on U.S. Pat. Nos. 4,315,513 and 4,393,873 for a percutaneous transport tube with a one way valve for gastric feeding, and is an expert on the subject of conditions and problems related to tube feeding.

Great efforts have been made by major corporations to provide balanced nutritional formulations for specific medical conditions to be used for tube feeding. Depending on the specific medical condition, the severity of the problem, and/or a moment in time, constipation may present serious additional medical problems. One of the major short comings of commercial premixed products is that they do not readily contain enough fiber. There are continuing on going efforts to create tube feeding formulas that will address this problem. As an example Novartis Nutrition has created IMPACT with Fiber. This product contains 250 calories per 250-ml can and only 2.5-mg of fiber. Also, liquid foods capable of passing through a tube are frequently high in calories and low in fiber. Patients who are on tube feedings usually do not get the optimal opportunity nor amount of physical activities. Such activity is important in stimulating proper functioning of the digestive tract. Therefore one can certainly surmise the additional importance of fiber in the diets of these individuals. The inventor also notes that some patients may have a high requirement for fiber whereas others do not. Therefore, one may administer excess calories in an attempt to provide adequate fiber. While it is known that water can be administered through feeding tubes it has been virtually impossible to administer adequate fiber. To that end patients receive far to many suppositories, enemas, and colonics. In addition, far too many chemically based laxative products are delivered through these tubes are.

Depending on the design of the particular tube, it may be expected that the viscosity of the feeding liquid may be a problem. With the consideration that her inventions possess a one-way valve it is far more difficult to use a viscous product than with the conventional latex tubes which have the additional options of using gravity flow techniques. Additionally, one must take into serious consideration the fact that nasal-gastric fed patients are more sensitive to being fed continuously, and or more frequently by the tube. Problem also may occur when the formulation is more viscous. This is especially true in traumatized and overly sensitive patients. Extensive feedings through these tubes may often irritate the throat. This has been addressed and taken most seriously by the inventor.

Whether it is for hospital, home, or travel like situations the ultimate solution for tube fed patients is to supplement the feeding regime with fiber-water rather than just plain water. Fiber-water, as described herein, is simple and accurate to administer. The fiber-water can be used as a standalone product or mixed with a given formula before delivering it to the patient as a single unit. Further, fiber-water can be added to the tube line in tandem with other supplementation (see U.S. Pat. No. 5,531,734 "Method of Altering Composition of Nutritional Product During Enteral Tube Feeding" and U.S. Pat. No. 5,533,973 "Alteration of Nutritional Product During Enteral Tube Feeding"). The inventor contemplates fiber-water in a number of different grades—that is with different quantities of fiber. The inventor further contemplates fiber-water, which is additionally a combination of safe water and one or more soluble as specific health conditions dictate. In this way both the type and strength can be selected that will provide the optimum amount of desired fiber to a given patient when the type and or quantity administered is adjusted to meet the patient's needs. It is further contemplated that the strengths and or types could each be uniquely indicated by a safe soluble food-grade color so that hospital personnel, other caregivers, or even the patient himself could readily recognize which grade of fiber-water was being administered. This would further ensure that the correct grade was used for a particular patient. Color has often been denoted to coincide with flavor. Thus, to a tube fed patient this addition of color might be pleasing, especially to a child patient, and provide a distraction from an unpleasant situation. Further, since these tubes are not always permanent, and if the fiber-water experience accomplishes the designed intent, and is both convenient and pleasant the inventor is hopeful that on going use of fiber-water will continue on a regular basis. The value of fiber-water will be carried forward to promote good health for life.

Having presented extensive information thus far on the benefits of both fiber and water it is therefore conceivably understood that future health problems may be addressed more readily and effectively. Further, it is the hope of the inventor that fiber-water will play a significant role in the future, whereby the ingestion of fiber-water on a daily basis will ameliorate, or altogether prevent, many health challenges.

Although the above discussion presupposes that the primary user of fiber-water would be an adult (over 21 years of age), infants, children and teens, as well, have significant fiber requirements. The younger population, as well as adults are victims of the American diet, which is notoriously deficient in fiber rich fruits and vegetables. Consciously or not, many parents have taught their children to reject foods that are brown, speckled or have significant textures. It is important that parents, or caregivers, become aware of the amount of fiber consumed by their children. In fact, the parent and or caregiver can monitor the fiber needs of their children on a regular basis since the fiber dose is controlled within a given amount of water. Thus it is possible to suspect a change in health status when a routinely sufficient amount of fiber-water used daily is either more than sufficient or insufficient.

Children can benefit from optimal hydration based on fiber-water. By helping control appetite we now may have discovered a way to address and control childhood and adult obesity as disclosed in U.S. Pat. No. 5,505,981 "Method for Imparting Ability of Preventing Obesity and Imparting Glucose Tolerance to Foods and Sugar Preparations Exhibiting Such Preventative Effects". It may even benefit individuals with such known eating disorders as anorexia or bulimia since these individuals typically drink water because it fills them up without providing calories. Fiber-water would at least help preserve proper functioning of the gastrointestinal tract while other treatment is hopefully undertaken.

Critically important may be the effect of fiber-water on both type one, type two (adult onset and juvenile) and or borderline diabetics as disclosed in U.S. Pat. No. 5,344,824 "Method for Reducing Insulin Secretion".

At every stage of life, fiber is vital to proper health, growth and development. Infants and toddlers require a regular and controlled source of fiber. After babies cease to breast-feed or use liquid formulas and move on to more varied "adult" solid foods, they often suffer a number of painful digestive episodes which makes them fussy and difficult. Because fiber-water provides an ideal source of hydration and fiber for such infants, it may be added to commercial formulas or used alone. Therefore, not only does it ensure adequate hydration, it also provides a consistent fiber source to guarantee regularity. It should be kept in mind that typical commercial baby foods may vary widely in the amount of fiber provided. Fiber-water provides an opportunity to lay the foundation of good habits of hydration and fiber intake. Additionally, it may be beneficial to add fiber-water to commercial baby food if a thinner consistency is desired.

Domestic animals, particularly cats and dogs, also suffer from problems with hydration and constipation. Dogs are omnivorous and will naturally consume some fruits and vegetables. However, refined dog foods tend to be remarkably deficient in vegetable fiber. Administering a source of fiber-water daily since dogs generally drink offered water can readily alleviate this problem. An alternative is to add the fiber water to dry kibble (or as an example, the "gravy" forming type) or even stirred into canned dog food. Because fiber-water is essentially flavorless, tests have shown that it has gone unnoticed by dogs, cats, and other animals. Cats also have serious dehydration and constipation problems. Cats are obligate carnivores and generally will not knowingly consume fruits or vegetables (other than valuable houseplants). Kidney failure is a common malady of geriatric cats resulting, in part, from inadequate hydration. Constant vomiting is a common feline problem brought on by their grooming during which they ingest significant quantities of fur. In the wild, cats ingest sufficient indigestible matter (bones, cartilage and tendons) to provide non-vegetable "fiber." With pet cats the owners are expected to mix fiber (generally psyllium) with the cat's food or administer petroleum-based laxatives. Neither alternative is particularly ideal. Fiber-water can be given as water or mixed with the cat's food to provide sufficient fiber to prevent both hairballs and constipation thus solving significant feline problems. It appears that reduction in vomiting positively contributes to the hydration of cats.

EXAMPLE 1

It has been estimated that adult fiber requirements are between about 10 grams and about 40 grams per day. Some experts have adopted a figure of around 25 grams. Obviously, the requirement for fiber is related to body size, weight and health status. Some attempts have been made to relate the requirement to weight. It has been estimated that between 50 and 300 mg. of fiber per kilogram of body weight per day. Fiber requirements can also be estimated from daily caloric intake. Current estimates call for about 25 grams per day for a 2,000-calorie diet (adequate for a 125 pound person) and about 37 grams for a 3,000-calorie diet (adequate for a 175 pound person). Both approaches yield roughly similar results since a heavier person usually has a greater caloric intake. These estimates should provide adequate fiber for even a person with a very fiber deficient diet.

To meet a 25 g of fiber per day requirement (with fiber-water being the sole fiber source as an example only) and using the rubric of 8 glasses of water (each glass equals approximately 250 ml of water) one should spread the 25 g over 2,000 ml (8×250 ml). Therefore, the fiber-water used should contain 12.5 mg/ml of soluble fiber or approximately 1.25% by weight fiber-water. For a daily caloric intake of 3,000 calories this translates to a fiber-water of about 2% by weight soluble fiber.

This analysis indicates that no fewer than two different "strengths" of fiber-water should be produced to allow a range of average persons receive both the optimum amount of water and fiber. In actual fact, it is convenient to produce a number of strengths (grades), for example, ranging from about 0.50% to 2.5%. This would allow a wide range of individuals to readily select a fiber-water strength that simultaneously supplies both the required amount of water and the required amount of fiber. For individuals who are not under constant medical monitoring the ingestion of fiber-water can be uniquely adapted to conform to ones lifestyle without compromising effectiveness and on an individual basis. Depending on individual needs and the desire to drink in relation to ability to drink the amount of fiber can be increased by using an appropriate "strength" of fiber-water to supply some or all of the required eight glasses of water. Of course, it is also possible that an individual is not able, nor does not intend, to spread out the fiber requirement over eight,(8), 8 oz. glasses throughout the day. Individuals do differ as to their specific habits, preferences, and do prefer to be in control of their choices. To that end for some it may be preferred to consume fiber-water at home—in the morning, evening, and or both—and not at work or throughout one's daily activities. For this and similar reasons, it is desirable to make multiple concentrated strengths (grades) of fiber-water ranging from 5% to even 10% by weight of fiber to reduce the number of daily doses needed and or desired. Thus, if one does not have fiber-water available all day, hydration can be assured by drinking plain safe water supplemented by a higher "grade" of fiber-water to reach the fiber requirement as described above. If necessary, the amount of fiber consumed can be reduced by using a lower "grade" of fiber-water—or even just plain safe water—for some of the daily-required eight glasses of water. It may also be advantageous to add a different food color to each grade so that the "strength" of the fiber-water can be identified at a glance. Colors can be used to indicate different strengths of fiber in the water, or color can be use to attract and or enhance desirability.

Fiber-water for testing according to the above scheme was produced by dissolving the required weights of a mixture of indigestible dextrins and partially hydrolyzed guar gum in purified water. The preferred dextrins or maltodextrins are prepared by controlled hydrolysis of vegetable starches (e.g. potato or corn) as is described in U.S. Pat. No. 5,620,873. The hydrolyzed guar gum is of the type discussed in U.S. Pat. No. 5,260,279 (available in the United States as BENEFIBER® from Novartis Nutrition of Minneapolis, Minn.; available in other countries as SUN-FIBER® from Taiyo of Japan). The resulting solution, in the strengths explained above, is essentially colorless and clear having the basic appearance of plain water. The liquid is either flavorless or may have a very slight "sweetness" depending on the strength of the particular solution and the proportion of the soluble fibers used. The partially hydrolyzed guar gum is essentially flavorless while the maltodextrin has a slight sweet taste. In addition, some individuals can detect a slightly different "mouth feel" because of the slight viscosity increase resulting from the soluble fibers.

However, for all practical purposes the resulting solution looks and behaves like bottled water and can readily be used in place of bottled water. If it is desired to ensure the microbial status of the fiber-water, it can be autoclaved or sterile filtered like plain water. Starting with a good quality drinking water preferably one with little or no sodium can ensure a safe and palatable product. Sodium-free safe water would be preferable to meet the standards of the Heart Association. Under the FDA regulations as long as one does not exceed one percent of the final product we can provide the addition of trace "essence" or flavor such as cherry, orange, grape, lime or lemon which can enhance palatability without adding any calories or otherwise detracting from the beneficial properties of the product. Without the approved additives fiber-water should look, behave and be used like high quality drinking water. To this end any "naturally occurring" water can be used as a starting. Thus, it is possible to start with a natural mineral water and produce "fiber mineral water." Such mineral waters are defined as bottled water containing not less than 250 parts per million total dissolved solids.

EXAMPLE 2

Infants also have distinct fiber requirements. Until recently, no specific guidelines for dietary fiber in children were available. Recommendations have recently been developed, based on age, weight and height of the child. It is now recommended that children older than two years consume a minimum amount of fiber equal to the age plus five grams a day. The recommended "safe dose" is between this and age plus ten grams a day. Above that symptoms of excess fiber (e.g., loose stool) may become apparent. It is the intent of the inventor to provide various grades of fiber-water provided in the present invention to enable a person or a caregiver to "titrate" the amount of fiber by looking for symptoms of excess fiber consumption. Since infants and small children are generally unable to directly tell us of their digestive distress, constipation and other results of inadequate fiber are often exhibited as fussiness or similar undesirable behavior. This is especially true when infants are just being weaned from fiber-free milk to a fiber containing diet. There can be significant advantage to providing a fiber source in the water consumed by the infant. Because infants have a constant requirement for water, the addition of fiber-water to the typical diet can provide a more constant, even source of fiber while ensuring adequate hydration. Further the use of fiber-water can ensure adequate fiber without adding significant calories—an inevitable consequence of other fiber sources. Consistent dietary fiber can provide for more even operation of the infant's digestive tract. In contrast, a more traditional infant diet that alternates between low fiber formula and high fiber "adult" foods may have, as an example, an uneven or cramping effect.

A useful amount of soluble fiber is ¼–1 gram per 8 oz (considerably lower concentration than for the adult fiber-water). The "baby fiber-water" is produced by dissolving the required amount of soluble fiber consisting of a mixture of partially hydrolyzed guar gum and inulin (FRUTAFIT® from Imperial-Sensus of Sugar Land, Tex. is a preferred inulin for this purpose) in safe (e.g., purified) water. The slight sweetness of the inulin makes the water especially palatable. The intent here is not to treat any specific diseases but to ameliorate constipation—and thus disease states known to cause constipation. For example, Hirshprung's syndrome is caused by a loss of motor cells in the lower rectum; therefore there is a loss of thrust. Children born with congenital problems or children still suffering from incompletely healed accidents benefit from fiber-water that provides bulk and hydration to help overcome serious constipation that may result from such causes. Actually babies are extremely sensitive to a variety of stresses and changes and get constipated as a result. Alternating bouts of regularity and or constipation is not uncommon. A baby's system may be under stress and that alone can be the cause. Infants can sense stress in their surroundings be it the home, etc.:

Dysfunctional homes where there is divorce, alcoholism, family abuse etc., may be noted in the babies refusal to eat, defecate, crying spells etc.

Changes in custodial care, baby sitters, new sibling(s), and/or a step-parent, etc.

Changes due to normal childhood illnesses, colds, flu, teething, fever, measles, mumps, chicken pox, etc. While these illnesses may not be the direct cause of constipation they may be the indirect cause. With illness come changes in eating, sleeping, behaviors, and habits.

Travel—when a babies environment is changed, from going to grandparents to international travel, sensitivities to the new, can throw off a system that is used to regularity. International travel bears with it the dehydration of long hours on an airplane etc. The future holds even more stressing travel such as space travel.

Accidents, also upset regular habits and can result in constipation.

Water probably can be given as early as one month, although usually started between 2–4 months after birth. In some instances fiber-water may be of especially significant value. Fiber-water can serve as a great pacifier and satisfy the babies need to suck and or be fed. This is especially valuable during "off feeding hours:" or in place of hard plastic and or rubber pacifiers that may cause harm. Of major importance is the fact that many babies who are given water are given water that is unsafe. Fiber-water insures that the water is safe. Diarrhea, which is often caused by contaminated water supplies, can be life threatening to infants. Therefore, there are great advantages to using safe bottled water for any infant and or infant formula, etc. Several commercial companies including GERBER® and BEACH-NUT® have bottled "baby water". Using safe packaged fiber-water is even better where it is desired to avoid excessive caloric intake. In the case of the "fat baby" the fiber-water may well do more than provide a low or non caloric-hydrating agent. The soluble fiber in fiber-water has been show to slow the absorption of fats and sugars (see U.S. Pat. No. 5,505,981). Therefore, the fiber-water may also help to counteract an overly rich diet.

As the infant becomes a toddler and moves towards more a more adult diet, the requirement for fiber increases. Fiber-water again serves as the ideal source of both hydration and fiber. Unlike sugar-laden soft drinks and/or fruit juices fiber-water does not add calories to the diet nor does it promote the potential addiction to sweets and/or "want to have sweets" to feel satisfied. Additionally, an abundance of sugar starting at an early age is now believed to be "the set up" for the many health challenges later in life. The most obvious being diabetes.

While fiber-water may be packaged in any container and under the conditions designated by governmental health standards the inventor considers the packaging of fiber-water for children, especially young children, to be packaged in flexible pouches or laminate boxes for several reasons, including the dangers of glass containers, or the "less likely to spill" of a wide mouth cup. Additionally, the child is less likely to put potentially dangerous ingredients and or small objects into a wide mouth drinking container thus creating potential dangers in swallowing the just mentioned. As with adult fiber-water, it is advantageous to provide the infant and child fiber-water in a number of "strengths" so that the amount of fiber administered can be readily monitored and appropriately adjusted on an individual basis. Again, it may be advantageous to add identifying color so that it is clear to the parent precisely which grade of fiber-water is being used. In the case of children the color is inherently appealing and may mitigate in favor of using transparent packaging so that the child can appreciate the color of the fiber-water being consumed. It is also conceivable that if the container is not transparent that a transparent straw may show the color, or that specific graphics and/or color on the container will relate to the strength (apart from the aesthetic appeal of the color or graphics).

The importance of creating a fiber-water for teenagers cannot be overlooked. Especially true if they have significant health issues. The inventor would be remiss if she did not at least mention this concern. This age group, in their search for independence, are most inclined to make their own selections and much of their drinking is away from home. They are most influenced by media and peers. A strong effort should be made to provide color, essences, and packaging to address this age group in their language.

It is permissible and often advantageous to blend an assortment of different soluble fibers to create any particular fiber-water. It is believed that the various soluble fibers have essentially identical properties when it comes to providing bulk and hydration to the stools. However, it is not yet clear which soluble fibers will prove superior in altering lipid or sugar absorption, etc. Of the soluble fibers presently available the indigestible dextrins, inulins and partially hydrolyzed guar gum appear to provide the most "water clear" solutions. However, many dextrins and inulins contain a small amount of a metabolizable component and have a slight sweet taste. Therefore, there can be an advantage of providing a portion of the soluble fiber in the form hydrolyzed guar gum or some other flavorless and totally non-metabolizable compound. Even though some of these materials may produce a less clear solution, a combination with a "clear" soluble fiber can yield a solution that is both high in fiber and clarity and low in sweetness or other taste. Other soluble fibers can be combined to realize the advantages of the different fibers. Inulins have a slightly sweet taste and while not appreciably metabolized by humans, bacteria in the colon metabolize inulins. In some cases such colonic metabolism may provide a distinct advantage and would mitigate towards including inulins in the mixture. Until the advent of fiber-water the advantage of a clear or nearly clear soluble fiber was not appreciated.

As mentioned above, it is anticipated that partial hydrolysis and fractional refining of the various soluble fibers mentioned above will rapidly lead to a greater variety of "water clear" soluble fibers.

The present invention discloses the hitherto unappreciated advantages of using fiber-water as an essentially non-caloric source of fiber and water. In other words a new dietary component that simultaneously provides hydration and dietary fiber. While the examples have dwelt with prepackaged, ready to drink fiber-water, there is nothing that precludes fiber-water from being prepared by the end user from a concentrated ready mixed source of soluble fiber, potable water and or with the additions of flavor and essences under FDA regulations. The soluble fiber can be in the form of a powder, slurry/suspension or a concentrated solution or syrup to which a predetermined quantity of water is added. In the past such fiber sources have been added to solid food items and to various beverages. However, such concentrated sources of fiber have never been used to prepare potable fiber-water for direct consumption as water In addition to the equivalents of the claimed elements, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope and spirit of the invention. The illustrated embodiment has been set forth only for the purposes of example and that should not be taken as limiting the invention. Therefore, it is to be understood that, within the scope of the appended claims, the invention may be practiced other than as specifically described herein.

I claim:

1. A water composition for consumption by humans and animals comprising:

between 0.1% and 10% by weight water-soluble indigestible fiber; and safe water, wherein fewer than 10 calories per 100 ml is metabolized by a human when consuming the water composition and wherein the water composition contains less than 500 mg./l of soluble salts and essentially no organic acids.

2. The water composition of claim 1 further comprising a soluble food grade color.

3. The water composition of claim 2, wherein the soluble food grade color acts as an indicator of an amount of the water soluble indigestible fiber contained in the water composition.

4. The water composition claim 1, wherein the water soluble indigestible fiber is selected from the group consisting of plant mucilage, plant gums, dextrins, maltodextrins, galactomannans, arabanogalactans, beta glucans, cellulose ethers, pectins, pectic material, water-soluble hemicellulose, inulin, alginates, agar, carrageenan, psyllium, guar gum, gum traganth, gum karya, gum ghatti, gum acacia, gum arabic, partially hydrolyzed products thereof and mixtures thereof.

5. The water composition claim 1, wherein the water-soluble indigestible fiber and water form an optically clear solution.

6. A water composition for consumption by humans and animals comprising:

between 0.1% and 10% by weight water-soluble indigestible fiber selected from the group consisting of dextrins, maltodextrins, galactomannans, cellulose ethers, inulin, alginates, agar, carrageenan, psyllium, guar gum, gum traganth, gum karya, gum ghatti, gum acacia, gum arabic, partially hydrolyzed products thereof and mixtures thereof; and safe water, wherein the water and the water-soluble indigestible fiber form an optically clear solution, wherein fewer than 10 calories per 100 ml are metabolized by a human when consuming the water composition and wherein the water composition contains a nutritionally insignificant amount of soluble minerals and essentially no organic acids.

7. The water composition of claim 6 further comprising a soluble food grade color.

8. The water composition claim 7, wherein the soluble food grade color acts as an indicator of an amount of the water soluble indigestible fiber contained in the water composition.

9. A water composition for consumption by humans and animals comprising:

between 0.1% and 10% by weight water soluble indigestible fiber selected from the group consisting of dextrins, maltodextrins, inulin, guar gum, partially hydrolyzed products thereof and mixtures thereof; and safe water, wherein the water and the water soluble indigestible fiber form an optically clear solution, wherein fewer than 10 calories per 100 ml are metabolized by a human when consuming the water composition and wherein the water composition contains a nutritionally insignificant amount of soluble minerals and essentially no organic acids.

10. The water composition claim 9 further comprising a soluble food grade color.

11. The water composition of claim 10, wherein the soluble food grade color acts as an indicator of an amount of the water soluble indigestible fiber contained in the water composition.

12. The water composition of claim 1, wherein said water-soluble fiber is selected to satisfy simultaneously both hydration requirements and fiber requirements when consumed.

13. The water composition of claim 1, wherein addition of said water-soluble fiber does not alter clarity of the water composition.

14. The water composition claim 1 formulated for managing constipation.

15. A method of managing bowel regularity comprising the step of ingesting a quantity of the water composition of claim 1.

16. A method of managing hemorrhoids comprising the step of ingesting a quantity of the water composition of claim 1.

17. A method of avoiding assimilation of toxic bowel compounds comprising the step of ingesting a quantity of the water composition of claim 1.

18. The water composition of claim 1 formulated for management of diabetes.

19. The water composition of claim 1 formulated for management of obesity.

20. The water composition of claim 1 formulated for appetite suppression.

21. The water composition of claim 1 formulated for lowering serum cholesterol levels.

22. The water composition of claim 2, wherein the soluble food grade color acts as an indicator of a type of the water-soluble indigestible fiber contained in the water composition.

23. The water composition of claim 6, wherein the water-like fluid contains fewer than 500 mg./l of soluble salts.

24. The water composition of claim 6, wherein said water-soluble fiber is selected to satisfy both hydration requirements and fiber requirements when consumed.

25. The water composition of claim 6, wherein addition of said water-soluble fiber does not alter clarity of the water composition.

26. The water composition of claim 6 formulated for managing constipation.

27. A method of managing bowel regularity comprising the step of ingesting a quantity of the water composition of claim 6.

28. A method of managing hemorrhoids comprising the step of ingesting a quantity of the water composition of claim 6.

29. A method of avoiding assimilation of toxic bowel compounds comprising the step of ingesting a quantity of the water composition of claim 6.

30. The water composition of claim 6 formulated for management of diabetes.

31. The water composition of claim 6 formulated for appetite suppression.

32. The water composition of claim 6 formulated for management of obesity.

33. The water composition of claim 6 formulated for lowering serum cholesterol levels.

34. The water composition of claim 10, wherein the soluble food grade color acts as an indicator of a type of the water-soluble indigestible fiber contained in the water composition.

35. A water composition for consumption by humans and animals comprising:
   between 0.1% and 10% by weight water-soluble indigestible fiber; and
   safe water, wherein fewer than 10 calories per 100 ml is metabolized by a human when consuming the water composition and wherein the water composition contains a nutritionally insignificant amount of soluble minerals and essentially no organic acids.

36. The water composition of claim 35, wherein said water-soluble fiber is selected to satisfy simultaneously both hydration requirements and fiber requirements when consumed.

37. The water composition of claim 35, wherein addition of said water-soluble fiber does not alter clarity of the water composition.

38. The water composition of claim 35 formulated for management of constipation.

39. A method of managing bowel regularity comprising the step of ingesting a quantity of the water composition of claim 35.

40. A method of managing hemorrhoids comprising the step of ingesting a quantity of the water composition of claim 35.

41. A method of avoiding assimilation of toxic bowel compounds comprising the step of ingesting a quantity of the water composition of claim 35.

42. The water composition of claim 35 formulated for management of diabetes.

43. The water composition of claim 35 formulated for management of obesity.

44. The water composition of claim 35 formulated for appetite suppression.

45. The water composition of claim 35 formulated for lowering serum cholesterol levels.

* * * * *

UNITED STATES PATENT AND TRADEMARK OFFICE
CERTIFICATE OF CORRECTION

PATENT NO. : 6,248,390 B1
DATED : June 19, 2001
INVENTOR(S) : Suzanne Jaffe Stillman It is certified that error appears in the above-identified patent and that said Letters Patent is hereby corrected as shown below:

<u>Title page,</u>
Item [56], References Cited, add the following U.S. PATENT DOCUMENTS,

| | | | |
|---|---|---|---|
| 4,444,761 | 4/24/1984 | Spiller | 514/57 |
| 4,447,532 | 5/8/1984 | Coker et al. | 435/99 |
| 4,834,990 | 5/30/1989 | Amer | 46/74 |
| 4,849,222 | 7/18/1989 | Broaddus | 424/738 |
| 4,911,889 | 3/27/1990 | Leland et al. | 422/26 |
| 4,988,530 | 1/29/1991 | Hoersten et al. | 426/577 |
| 4,996,063 | 2/26/1991 | Inglett | 426/21 |
| 5,032,411 | 7/16/1991 | Stray-Gundersen | 426/74 |
| 5,082,673 | 1/21/1992 | Inglett | 426/21 |
| 5,108,774 | 4/28/1992 | Mills et al. | 426/599 |
| 5,149,541 | 9/22/1992 | Leis, Jr. et al. | 424/489 |
| 5,162,128 | 11/10/1992 | Mills et al. | 426/599 |
| 5,219,570 | 6/15/1993 | Barbera | 424/738 |
| 5,225,219 | 7/6/1993 | Inglett | 426/28 |
| 5,229,117 | 7/20/1993 | Leland et al. | 424/738 |
| 5,229,172 | 7/20/1993 | Cahalan et al. | 427/536 |
| 5,344,824 | 9/6/1994 | Ohkuma et al. | 514/58 |
| 5,358,729 | 10/25/1994 | Ohkuma et al. | 426/567 |
| 5,364,652 | 11/15/1994 | Ohkuma et al. | 426/549 |
| 5,380,717 | 1/10/1995 | Ohkuma et al. | 514/58 |
| 5,430,141 | 7/4/1995 | Ohkuma et al. | 536/103 |
| 5,447,730 | 9/5/1995 | Greenleaf | 424/680 |
| 5,472,732 | 12/5/1995 | Ohkuma et al. | 426/658 |
| 5,505,981 | 4/9/1996 | Wakabayashi et al. | 426/658 |
| 5,519,011 | 5/21/1996 | Wakabayashi et al. | 514/58 |
| 5,587,197 | 12/24/1996 | Meada et al. | 426/658 |
| 5,620,873 | 4/15/1997 | Ohkuma et al. | 435/99 |
| 5,755,688 | 5/26/1998 | Piontek et al. | 604/83 |
| 5,851,578 | 12/22/1998 | Gandhi | 426/590 |
| 5,958,497 | 9/28/1999 | Grimm et al. | 426/596 |
| 5,968,365 | 10/19/1999 | Laurenzo et al. | 210/641 |
| 5,976,603 | 11/2/1999 | Kota et al. | 426/590 |
| 5,997,917 | 12/7/1999 | Uchida et al. | 426/96 |
| 6,004,610 | 12/21/1999 | Wang et al. | 426/599 |
| 6,020,016 | 2/1/2000 | Castleberry | 426/590 |

UNITED STATES PATENT AND TRADEMARK OFFICE
CERTIFICATE OF CORRECTION

PATENT NO. : 6,248,390 B1
DATED : June 19, 2001
INVENTOR(S) : Suzanne Jaffe Stillman It is certified that error appears in the above-identified patent and that said Letters Patent is hereby corrected as shown below:

Title page (cont'd),
Add the following references:

Takashi Ide, et al., "Hypolipidemic Effects of Guar Gum and Its Enzyme Hydrolysate in Rats Fed Highly Saturated Fat Diets," Ann Nutr Metab 1991;35:34-44 (abstract).
M. Kamen, et al., "Reduction in Diarrhea Incidence by Soluble Fiber in Patients Receiving Total or Supplemental Enteral Nutrition," Dept. of Surgery, Ruhr University, Bochum, Germany, 6/20/1994; JPEN, 18:486-90, 1994 (abstract).
Gary A. Weaver et al., "Dietary Guar Gum Alters Colonic Microbial Fermentation in Azoxymetane-Treated Rats," J of Nutrition 126(8) : 1979- 1991 (abstract).
Hidehisa Takahashi et al., "Effect of Partially Hydrolyzed Guar Gum on Fecal Output in Human Volunteers," Nutrition Research, Vol. 13, pp. 649-57, 1993 (abstract).
A. Golay et al., "The effect of a liquid supplement containing guar gum and fructose on glucose tolerance in non-insulin-dependent diabetic patients," Nutr. Metab. Cardiovasc. Dis (1995) 5:141-148 (abstract).

Hidehisa Takahashi et al., "Effect of Liquid Diets With or Without Partially Hydrolyzed Guar Gum on Intestinal Microbial Flora and Function of Rats," Nutrition Research, Vol. 15, No. 4, pp. 527-536, 1995 (abstract).
Hidehisa Takahashi et al., "Influence of intact and partially hydrolyzed guar gum on iron utilization in rats fed on iron-deficient diets,", Comp. Biochem. Physiol. Vol. 109A, No. 1, pp. 75-82, 1994 (abstract).
Hidehisa Takahashi et al., "Influence of Partially Hydrolyzed Guar Gum on Constipation in Women," J. Nutr. Sc. Vitamental. 40, pp. 251-259, 1994 (abstract).
A. Golay et al., "The effect of a liquid supplement containing guar gum and fructose on glucose tolerance in non-insulin-dependent diabetic patients," NMCD Nutrition, Metabolism and Cardiovascular Diseases, Vol. 5, No. 2, June 1995, pp. 141-147 (abstract).
Hiroshi Hara et al., "Increases in calcium absorption with ingestion of soluble dietary fibre, guar-gum hydrolysate, depend on the casecum in partially nephrectomized and normal rats," British Journal of Nutrition (1996), 76, pp. 773-784 (abstract).
Brochures by Imperial Sensus LLC, "Product Data Sheets," "Facts about Inulin/FOS," "Frutafit Nutritional Information," "What is Frutafit."
Joanne Slavin, "Commercially Available Enteral Formulas with Fiber and Bowel Function Measures," Nutrition in Clinical Practice 5:247-250, December 1990.
Y. Ueda et al., "Effects of Indigestible Dextrin on Blood Glucose and Insulin Levels after Various Sugar Loads In Rats," J.Jpn. Soc. Nutr. Food Sci. 1993 (46) 131-137 (abstract, Fig. 1 and Tables1-4).
John E. Greenleaf, "Problem: thirst, drinking behavior, and involuntary dehydration," Medicine and Science In Sports and Exercise, Vol. 24, No. 6, pp. 645-656, 1992.

UNITED STATES PATENT AND TRADEMARK OFFICE
CERTIFICATE OF CORRECTION

PATENT NO. : 6,248,390 B1
DATED : June 19, 2001
INVENTOR(S) : Suzanne Jaffe Stillman It is certified that error appears in the above-identified patent and that said Letters Patent is hereby corrected as shown below:

Elsworth R. Buskirk et al., eds., "Body Fluid Balance," CRC Press, 1966, pp. 1-17.
Kazuhiro Ohkuma et al., "Pyrolysis of Starch and Its Digestibility by Enzymes --- Characterization of Indigestibility Dextrin---," Matsutani Chemical Resarch Laboratories, Denpun Kagaku, 1990 (37) 107-114 (abstract, Figs. 1-7, Tables 1-5).
Brochure by Matsutani Chemical Industry, "Fibersol-2-Physiological Attributes," 2-16-1999.
Brochure by Matsutani America, Inc., "Matsutani's Products and Their Functionalities," 5-1999.
Y. Kishimoto et al., "Hypocholesterolemic Effect of Sodium Propionate," J. Nutri. Sci. Vitaminol, Vol. 41, No. 1, 1995, pp. 77, 78.
Novartis Nutritional Corporation, "Benefiber Nutritional Data," 3-1999.
Novartis Nutritional Corporation, "Novartis Nutrition Foodservice Products, 1/31/2000.
Brochure by Matsutani Chemical Industry Co., Ltd., "Fibersol 2."
Pamphlet by Imperial Sensus, LLC, "Inulin, A Natural Non-Digestible Carbohydrate Having Healthy Influences For Preventing Disease -- Occurrence, History, Preparation, Safety, Physiology and Related Health Implications," Version 23-10.29.99, 1997, 1998, 1999.

Signed and Sealed this

Thirteenth Day of May, 2003

JAMES E. ROGAN
*Director of the United States Patent and Trademark Office*

US006248390C1

(12) EX PARTE REEXAMINATION CERTIFICATE (7697th)
United States Patent
Stillman

(10) Number: US 6,248,390 C1
(45) Certificate Issued: Aug. 24, 2010

(54) FIBER-WATER-WATER CONTAINING SOLUBLE FIBER

(76) Inventor: Suzanne Jaffe Stillman, 264 S. Linden Dr., Beverly Hills, CA (US) 90212

Reexamination Request:
No. 90/009,253, Aug. 15, 2008

Reexamination Certificate for:
Patent No.: 6,248,390
Issued: Jun. 19, 2001
Appl. No.: 09/510,400
Filed: Feb. 22, 2000

Certificate of Correction issued May 13, 2003.

(51) Int. Cl.
*A23L 2/00* (2006.01)
*A23L 2/54* (2006.01)

(52) U.S. Cl. .................. 426/590; 426/74; 426/648; 426/590; 426/73; 514/40

(58) Field of Classification Search .................. None
See application file for complete search history.

(56) References Cited

U.S. PATENT DOCUMENTS

| | | |
|---|---|---|
| 2,224,252 A | 12/1940 | Callaway |
| 3,009,859 A | 11/1961 | Laborit et al. |
| 3,111,641 A | 11/1963 | Sperti et al. |
| 3,227,562 A | 1/1966 | Houghtaling et al. |
| 3,337,404 A | 8/1967 | Polli et al. |
| 3,564,740 A | 2/1971 | Calfee |
| 3,908,024 A | 9/1975 | Wankler |
| 3,939,283 A | 2/1976 | Billington |
| 4,034,493 A | 7/1977 | Bail |
| 4,042,684 A | 8/1977 | Kahm |
| 4,154,814 A | 5/1979 | Hand et al. |
| 4,167,587 A | 9/1979 | Danforth |
| 4,187,194 A | 2/1980 | Wellman et al. |
| 4,211,668 A | 7/1980 | Tate |
| 4,217,370 A | 8/1980 | Rawlings et al. |
| 4,283,432 A | 8/1981 | Mitchell et al. |
| 4,309,417 A | 1/1982 | Staples |
| 4,315,513 A | 2/1982 | Nawash et al. |
| 4,393,873 A | 7/1983 | Nawash et al. |
| 4,444,761 A | 4/1984 | Spiller |
| 4,447,532 A | 5/1984 | Coker et al. |
| 4,448,770 A | 5/1984 | Epting, Jr. |
| 4,497,793 A | 2/1985 | Simkin |
| 4,689,235 A | 8/1987 | Barnes et al. |
| 4,711,784 A | 12/1987 | Yang |
| 4,738,856 A | 4/1988 | Clark |
| 4,749,575 A | 6/1988 | Rotman |
| 4,777,042 A | 10/1988 | Toda et al. |
| 4,778,677 A | 10/1988 | Ebbesen |
| 4,784,861 A | 11/1988 | Gori |
| 4,834,990 A | 5/1989 | Amer |
| 4,849,222 A | 7/1989 | Broaddus |
| 4,911,889 A | 3/1990 | Leland et al. |
| 4,953,572 A | 9/1990 | Rose et al. |
| 4,988,530 A | 1/1991 | Hoersten et al. |

(Continued)

FOREIGN PATENT DOCUMENTS

| | | |
|---|---|---|
| FR | 2586532 | 3/1987 |
| JP | 59051741 A | 3/1984 |
| JP | 10-09520 | 1/1989 |
| JP | H02-154673 | 6/1990 |
| JP | 02-154673 | 6/1990 |
| JP | 4-311378 A | 11/1992 |
| JP | H5-17503 | 1/1993 |
| JP | 05-017503 | 1/1993 |
| JP | H06-90703 | 4/1994 |
| JP | 06-090703 | 4/1994 |
| JP | 6-100442 | 4/1994 |
| JP | 8-275752 | 10/1996 |
| JP | 9-020660 | 1/1997 |
| JP | 09059138 A | 3/1997 |
| JP | 09-245492 | 3/1999 |

(Continued)

OTHER PUBLICATIONS

Information Access Company, http://www.funding-universe.com, Company History, pp. 1–4, Nov. 17, 2009.*
Delta Communications Group, htto://www.delta-comm.com, 1 page, Nov. 17, 2009.*
Chemical Database: picloram, EnvironmentalChemistry.com, http://environmentalchemistry.com, pp. 1–3, Nov. 17, 2009.*
Morrison and Boyd, "Acidity of phenols", pp. 797–799, in Organic Chemistry, $3^{rd}$ ed., Allyn and Bacon, Inc., Boston, 1973.*

(Continued)

*Primary Examiner*—Brenda Brumback

(57) ABSTRACT

A shelf stable, ready to use, essentially tasteless and odorless water-like fluid for humans/animals comprised of safe water and a significant quantity of one or more water-soluble dietary fibers. Fiber-water is intended to be consumed by drinking or by enteral feeding alone, and/or in combination. The inventive liquid may be consumed directly hot or cold or after use, at any required temperature, in the preparation/reconstitution of beverages or liquid food product (e.g. coffee, tea, concentrates such as "HAWAIIAN PUNCH®", frozen concentrates such as lemonade/orange juice, soups and pet food). It can be used to enrich foods with soluble fiber through cooking, moistening, reconstituting or imbibing dried foods (e.g. oatmeal, rice, dried fruits, powdered soups, powdered beverages, powdered milks, nutritional shakes, "GATORADE®/ TANG®/KOOL-AID®" products, gelatins, custards, puddings, and pet food). Fiber-water can be consumed in the frozen state either indirectly by adding it to a beverage as a cube or crushed "ice", or directly by licking a frozen "POPSICLE®"product). Fiber-water is safe water fiber enriched intending to be a replacement and/or adjunct to other water to ensure proper hydration while at the same time provide significant soluble fiber. Depending on the soluble fiber(s) used, and the user's individual metabolism, the invention is non-calorie or extremely low in calories. The soluble fiber(s) used are proven to moderate the postprandial rise in blood glucose (diabetes), address weight loss (obesity), lower scrum cholesterol level (cardiovascular/heart), and address constipation and bowel regularity (colon cancer).

(Continued)

U.S. PATENT DOCUMENTS

| | | |
|---|---|---|
| 4,996,063 A | 2/1991 | Inglett |
| 5,002,934 A | 3/1991 | Norton et al. |
| 5,009,819 A | 4/1991 | Popescu et al. |
| 5,019,400 A | 5/1991 | Gombotz et al. |
| 5,019,594 A | 5/1991 | Wurtman et al. |
| 5,024,842 A | 6/1991 | Edgren et al. |
| 5,032,411 A | 7/1991 | Stray-Gundersen |
| 5,051,261 A | 9/1991 | McGinity et al. |
| 5,055,460 A | 10/1991 | Friedlander |
| 5,077,057 A | 12/1991 | Szoka, Jr. |
| 5,082,673 A | 1/1992 | Inglett |
| 5,108,774 A | 4/1992 | Mills et al. |
| 5,126,332 A | 6/1992 | Ohta et al. |
| 5,149,541 A | 9/1992 | Leis, Jr. et al. |
| 5,162,128 A | 11/1992 | Mills et al. |
| 5,178,896 A | 1/1993 | Langner |
| 5,209,978 A | 5/1993 | Kosaka et al. |
| 5,215,750 A | 6/1993 | Keane, II |
| 5,219,570 A | 6/1993 | Barbera |
| 5,223,268 A | 6/1993 | Stetski et al. |
| 5,225,219 A | 7/1993 | Inglett |
| 5,229,117 A | 7/1993 | Leland et al. |
| 5,229,172 A | 7/1993 | Cahalan et al. |
| 5,260,279 A | 11/1993 | Greenberg |
| 5,260,873 A | 11/1993 | Hishinuma |
| 5,270,297 A | 12/1993 | Paul et al. |
| 5,273,754 A | 12/1993 | Mann |
| 5,294,458 A | 3/1994 | Fujimori |
| 5,294,606 A | 3/1994 | Hastings |
| 5,300,310 A | 4/1994 | Elsen |
| 5,344,824 A | 9/1994 | Ohkuma et al. |
| 5,358,729 A | 10/1994 | Ohkuma et al. |
| 5,364,652 A | 11/1994 | Ohkuma et al. |
| 5,374,444 A | 12/1994 | Langner |
| 5,378,474 A | 1/1995 | Morella et al. |
| 5,380,717 A | 1/1995 | Ohkuma et al. |
| 5,397,786 A | 3/1995 | Simone |
| 5,405,836 A | 4/1995 | Richar et al. |
| 5,422,352 A | 6/1995 | Astrup |
| 5,430,141 A | 7/1995 | Ohkuma et al. |
| 5,447,730 A | 9/1995 | Greenleaf |
| 5,456,985 A | 10/1995 | Zgoulli et al. |
| 5,458,893 A | 10/1995 | Smith |
| 5,472,732 A | 12/1995 | Ohkuma et al. |
| 5,505,981 A | 4/1996 | Wakabayashi et al. |
| 5,516,535 A | 5/1996 | Heckert et al. |
| 5,519,011 A | 5/1996 | Wakabayashi et al. |
| 5,531,734 A | 7/1996 | Geckle et al. |
| 5,533,973 A | 7/1996 | Piontek et al. |
| 5,543,405 A | 8/1996 | Keown et al. |
| 5,550,113 A | 8/1996 | Mann |
| 5,558,897 A | 9/1996 | Goldman |
| 5,567,424 A | 10/1996 | Hastings |
| 5,571,441 A | 11/1996 | Andon et al. |
| 5,587,197 A | 12/1996 | Maeda et al. |
| 5,597,604 A | 1/1997 | Chalupa et al. |
| 5,605,697 A | 2/1997 | Asano et al. |
| 5,612,026 A | 3/1997 | Diehl |
| 5,620,873 A | 4/1997 | Ohkuma et al. |
| 5,653,996 A | 8/1997 | Hsu |
| 5,672,301 A | 9/1997 | Orly et al. |
| 5,681,606 A | 10/1997 | Hutchison et al. |
| 5,698,437 A | 12/1997 | Matsuda et al. |
| 5,700,484 A | 12/1997 | Chauffard et al. |
| 5,721,345 A | 2/1998 | Roberfroid et al. |
| 5,753,295 A | 5/1998 | Goldman |
| 5,755,688 A | 5/1998 | Piontek et al. |
| 5,776,524 A | 7/1998 | Reinhart |
| 5,780,060 A | 7/1998 | Levy et al. |
| 5,789,393 A | 8/1998 | Dressman et al. |
| 5,792,754 A | 8/1998 | Green et al. |
| 5,810,018 A | 9/1998 | Monte |
| 5,824,353 A | 10/1998 | Tsunoda et al. |
| 5,851,578 A | 12/1998 | Gandhi |
| 5,880,109 A | 3/1999 | Nakamura et al. |
| 5,891,465 A | 4/1999 | Keller et al. |
| 5,900,251 A | 5/1999 | Raissen |
| 5,904,851 A | 5/1999 | Taylor et al. |
| 5,922,346 A | 7/1999 | Hersh |
| 5,922,350 A | 7/1999 | Janoff et al. |
| 5,935,826 A | 8/1999 | Blue et al. |
| 5,958,456 A | 9/1999 | Baichwal et al. |
| 5,958,491 A | 9/1999 | Knueven |
| 5,958,497 A | 9/1999 | Grimm et al. |
| 5,962,015 A | 10/1999 | Delrieu et al. |
| 5,968,365 A | 10/1999 | Laurenzo et al. |
| 5,968,569 A | 10/1999 | Cavadini et al. |
| 5,972,415 A | 10/1999 | Brassart et al. |
| 5,976,603 A | 11/1999 | Kota et al. |
| 5,977,175 A | 11/1999 | Lin |
| 5,985,282 A | 11/1999 | Haveson |
| 5,989,574 A | 11/1999 | Slavin |
| 5,993,880 A | 11/1999 | Frost et al. |
| 5,997,917 A | 12/1999 | Uchida et al. |
| 6,001,554 A | 12/1999 | Boyle et al. |
| 6,004,610 A | 12/1999 | Wang et al. |
| 6,007,838 A | 12/1999 | Alving et al. |
| 6,007,872 A | 12/1999 | Lindhe et al. |
| 6,013,622 A | 1/2000 | Bruno et al. |
| 6,017,550 A | 1/2000 | Berk et al. |
| 6,020,002 A | 2/2000 | Myers et al. |
| 6,020,016 A | 2/2000 | Castleberry |
| 6,022,500 A | 2/2000 | John et al. |
| 6,022,525 A | 2/2000 | Sutton et al. |
| 6,030,605 A | 2/2000 | D'Ameila et al. |
| 6,033,713 A | 3/2000 | Sheldon |
| 6,033,888 A | 3/2000 | Batich et al. |
| 6,039,952 A | 3/2000 | Sunvold et al. |
| 6,042,854 A | 3/2000 | Morris et al. |
| 6,077,504 A | 6/2000 | Vesley et al. |
| 6,077,872 A | 6/2000 | Yu et al. |
| 6,102,224 A | 8/2000 | Sun et al. |
| 6,120,803 A | 9/2000 | Wong et al. |
| 6,133,323 A | 10/2000 | Hayek |
| 6,180,099 B1 | 1/2001 | Paul |
| 6,180,131 B1 | 1/2001 | Sunvold et al. |
| 6,190,591 B1 | 2/2001 | Van Lengerich |
| 6,193,999 B1 | 2/2001 | Gennadios |
| 6,204,291 B1 | 3/2001 | Sunvold et al. |
| 6,235,320 B1 | 5/2001 | Daravingas et al. |
| 6,248,390 B1 | 6/2001 | Stillman |
| 6,261,589 B1 | 7/2001 | Pearson et al. |
| 6,265,450 B1 | 7/2001 | Asami et al. |
| 6,296,892 B1 | 10/2001 | Elseviers et al. |
| 6,313,558 B1 | 11/2001 | Abukawa et al. |
| 6,328,967 B1 | 12/2001 | Rivera |
| 6,355,274 B1 | 3/2002 | Dartey et al. |
| 6,365,209 B2 | 4/2002 | Cherukuri |
| 6,368,629 B1 | 4/2002 | Watanabe et al. |
| 6,368,633 B1 | 4/2002 | Lou et al. |
| 6,383,534 B1 | 5/2002 | Dyrr et al. |
| 6,399,090 B1 | 6/2002 | Shehadeh |
| 6,399,124 B1 | 6/2002 | Lesens et al. |
| 6,403,657 B1 | 6/2002 | Hinz |
| 6,406,730 B1 | 6/2002 | Banyard et al. |
| 6,410,061 B1 | 6/2002 | Morre et al. |
| 6,410,521 B1 | 6/2002 | Mundy et al. |
| 6,410,522 B1 | 6/2002 | Ruenberg |
| 6,410,685 B1 | 6/2002 | Masuyama et al. |
| 6,413,558 B1 | 7/2002 | Weber et al. |
| 6,416,800 B1 | 7/2002 | Weber et al. |

| | | |
|---|---|---|
| 6,416,806 B1 | 7/2002 | Zhou |
| 6,420,350 B1 | 7/2002 | Fleischner |
| 6,436,453 B1 | 8/2002 | Van Lengerich et al. |
| 6,468,568 B1 | 10/2002 | Leusner et al. |
| 6,500,463 B1 | 12/2002 | Van Lengerich |
| 6,531,156 B1 | 3/2003 | Clark et al. |
| 6,544,568 B2 | 4/2003 | La Droitte et al. |
| 6,558,718 B1 | 5/2003 | Evenson et al. |
| 6,620,445 B1 | 9/2003 | Knueven |
| 6,723,358 B1 | 4/2004 | Van Lengerich |
| 6,758,715 B2 | 7/2004 | Banks |
| 6,953,593 B2 | 10/2005 | Kuhrts |
| 7,238,380 B2 | 7/2007 | Stillman |
| 2002/0132780 A1 | 9/2002 | Heisey et al. |
| 2005/0211768 A1 | 9/2005 | Stillman |
| 2007/0009576 A1 | 1/2007 | Stillman |
| 2007/0160735 A1 | 7/2007 | Stillman |
| 2008/0014327 A1 | 1/2008 | Stillman |

FOREIGN PATENT DOCUMENTS

| | | |
|---|---|---|
| JP | 11-512604 A | 11/1999 |
| JP | 2000-232855 | 8/2000 |
| JP | 2001-509007 A | 7/2001 |
| WO | WO 97/11614 A1 | 4/1997 |
| WO | WO 98/19564 A1 | 5/1998 |
| WO | WO 01/62108 | 8/2001 |
| WO | WO 01/70591 A1 | 9/2001 |

OTHER PUBLICATIONS

Total dissolved solids in Drinking–water, Guidelines for drinking–water quality, $2^{nd}$ ed. vol. 2, Health criteria and other supporting information. World Health Organization, Geneva, 1996.*

Electronic code of Federal Regulations, Title 21: Food and Drugs, Part 165.110 Bottled Water, Jul. 6, 2009.*

BetaCote™ Technical Information, Lycored Natural Products Industries, accessed via the internet on Sep. 18, 2009 att URL <http://www.lycored.com/web/content/betacote–tech.asp.

A. Golay et al., "The effect of a liquid supplement containing guar gum and fructose on glucose tolerance in non–insulin–dependent diabetic patients", Nutr Metab Cardiovasc Dis (1995) 5:141–148.

"Hypochelesterolemic Effect of Sodium Proprionate", J. Nutri. Sci. Vitaminol., vol. 41, No. 1, 1995, pp. 77–78, Kishimoto, et al.

Cordoba, et al., "Chondroitin Sulfate and Other Sulfate Containing Chondroprotective Agents . . . ", Osteoarthritis and Cartilage, 2003 v. 11 p. 228.

Markovich, "Physiological Roles and Regulation of Mammalian Sulfate Transporters", Physiological Reviews, 2001 v. 81 No. p. 1499.

Hoffer, et al., "Sulfate Could Mediate The Therapeutic Effect of Glucosamine Sulfate", Metabolism 2001, v. 50 p. 767.

Hannan, "Effect of Dietary Protein on Bone Loss in Elderly Men and Women", J. of Bone and Mineral Research, 2000 v. 15 p. 2504.

ProductScan Online, Worldwide beverage Industry in which products are marketed as containing Fiber or as being a good source of Fiber, 137 Full Reports, Mar. 1, 2003.

ProductScan Online, Asian Beverage Industry in which products are marketed as fruit and Fruit flavored drinks, 154 Full Reports, Dec. 30, 2002.

ProductScan Online, German Beverage Industry in which products are marketed as fruit and Fruit flavored drinks, 127 Full Reports, May 13, 2002.

Takashi Ide, et al., "Hypolipidemic Effects of Guar Gum and It's Enzyme Hydrolysale in Rats Fed Highly Saturated Fat Diets", Ann Nutr. Metab, 1991; 35:34–44 (abstract).

"Reduction in Diarrhea Incidence by Soluble Fiber in Patients Receiving Total or Supplemental Enteral Nutrition," Dept. of Surgery, Ruhr University, Bochum Gammany, Jun. 20, 1994; JPEN, 18:486–90, 1994 (abstract), H. H. Homann et al.

Gary A. Weaver, et al., "Dietary Guar Gum Alters Colonic Microbial Fermentation In Azoxymetana–Treated Rats", J of Nutrition 126(8): 1979–1991 (abstract).

Hidehisa Takahashi, et al., "Effect of Partially Hydrolyzed Guar Gum on Fecal Output in Human Volunteers,"Nutrition Research, vol. 13, pp. 649–657, 1993 (abstract).

Hidehisa Takahashi, et al., "Effect of Liquid Diets with or without partially hydrolyzed Guar. Gum on Intestinal Microbial Flora and Function of Rats", Nutrition Research, vol. 15, No. 4, pp. 527–536,1995 (abstract).

Hidehisa Takahashi, et al., "Influence of Intact and Partially Hydrolysed Guar Gum on Iron Utilization in Rats Fed On Iron–Deficient Diets", Comp. Biochem. Physical. vol. 109A, No. 1, pp. 75–82 (1994) abstract.

Hidehisa Takahashi, et al., "Influence of Partially Hydrolyzed Guar Gum on Constipation in Women", Vitamental., vol. 40, p. 251–259 (1994).

Hiroshi Hara, et al., Increases in Calcium Absorption With Ingestion of Soluble Dietary Fibre, Guar–Gum Hydrolysate, Depend on the Casecum in Partially Nephrectomized and Normal Rats, British Journal of Nutrition (1996) pp. 773.

Kazuhiro Ohkuma, et al., "Pyrolysis of Starch and Its Digestibility by Enzymes—Characterization of Indigestibility Dextrin—", Matsutani Chemical Research Laboratories Denpun Kagaku, 1990 (37) 107–114.

Brochure by Matsutani Chemical Industry, "Fibersol–2–Physiological Attributes", Feb. 16, 1999.

Brochure by Matsutani America, Inc., Matsutani's Product & Their Functionalities, May 1999.

Brochures by Imperial Sensus LLC, Facts About Insulin/FOS, "Fruitafit Nutritional Information", What is Fruitafit?, 1999.

Novartis Nutrition Corporation, "Benefiber Nutritional Data", Mar. 1999.

Novartis Nutrition Corporation, "Novartis Products", Jan. 31, 2000.

Pamphlet by Imperial Sensus, LLC, "Inulin, A Natural Non–Digestible Carbohydrate Having Healthy Influences For Preventing Disease—Occurrence, History, Preparation, Safety, Physiology and Related Health Implications", Version 23–10.29.99, 1997, 1998, 1999.

Elsworth R. Buskirk, et al., "Body Fluid Balance" CRC Press, 1966, pp. 1–17.

Flavor Encapsulation: A Convergence of Science and Art, Food and Technology, Jul. 2004, vol. 58, No. 7, Porzio et al.

Novel Encapsulation System Provides Controlled Release of Ingredients, Nov. 2003, vol. 57, No. 11, Shifer et al.

Goldschlager Article from http://www.cockeyed.com/inside/goldschlager/goldschlager.html, 2004.

Orbitz Article from http://www.bevnet.com/reviews/orbitz, 2004.

Joanne Slavin, "Commercially Available Enteral Formula With Fiber and Bowel Function Measures", Nutrition in Clinical Practice, vol. 5 pp. 247–250, Dec. 1990.

Y. Ueda, et al., "Effects of Ingestible Dextrin on Blood Glucose and Insulin Levels After Various Sugar Loads in Rats", Japan Nutritional Food Science, 1993, p. 46.

John E. Greenleaf "Problem: Thirst, Drinking Behavior and Involuntary Dehydration" Medicine and Science in Sports and Exercise, pp. 645–656.

Kazuhiro Ohkuma, et al., Pyrolysis of Starch and Its Digestibility by Enzymes–Characterization of Indigestibility Dextrin–Matsutani Chemical Research Laboratories, Denpun Kagaku, 1990 (37) 107–114 (abstract) Figs. 1–7, Tablets 1–5.

A.J. Vince, et al., The effect of lactulose, pectin, arabinogalactan and cellulose . . . , British Journal of Nutrition, 1990, vol. 63, pp. 17–26, London.

R. Robinson, et al., Effects of Dietary Arabinogalactan on Gastrointestinal and Blood . . . , Journal of the American College of Nutrition, 2001, vol. 20, 279–285.

http://diabets.webmd.com/is–there–a–diabetes–cure (accessed Jan. 21, 2009).

Deis, R., "Dietary Fiber: A Healthy Discussion," Food Product Design. Jan. 1999.

Y. Ueda, et al., "Effects of Indigestible Dextrin on Blood Glucose and Urine C–peptide Levels Following Sucrose Loading", J. Japan Diab. Soc., 1993 (36), 715–723.

M. Nummura, et al., "Effect of Dietary Fibers on the Deffusion of Glucose and Metal Ions through Cellulose Membrane", J. Japan Soc. Clin. Nutri., 1992, 141–147.

Yuka Kishimoto, et al., "Effects of Intravenous Injection and Intraperitoneal Continual Administration of Sodium Propionate on Serum Cholesterol Levels in Rats", J. Nutri. Sci. Vitaminol., 1995, 73–81.

Yuka Kishimoto, et al., "Hypocholesterol Effect of Dietary Fiber: Relation to Intestinal Fermentation and Bile Acid Excretion", J. Nutr. Sci. Vitaminol., 1995, 151–161.

K. Tokunaga, "Effects of a Food for Specified Health Use (FOSHU) Which Contains Indigestible Dextrin as an Effective Ingredient on Glucose and Lipid Metabolism", J. Japan Diab. Soc., 1999, 61–65.

S. Wakabayashi, et al., "Effects of Indigestible Dextrin on Sugar Tolerance: II. Effect of Continuous Administration in Rats Fed on a High Sucrose Diet", J. Japan Diab. Soc., 1992, 873–880.

S. Wakabayashi, "The Effects of Indigestible Dextrin on Sugar Tolerance: III. Improvement in Sugar Tolerance by Indigestible Dextrin on the Impaired Glucose Tolerance Model", Folia Endocrinol., 1993, 594–608.

S. Wakabayashi, "The Effects of Indigestible Dextrin on Sugar Tolerance: I. Studies on Digestion–Absorption and Sugar Tolerance", Folia Endocrinol., 1992, 623–635.

S. Wakabayashi, "Effects of Indigestible Dextrin on Glucose Tolerance in Rats" Journal of Endocrinology, 1995, 533–538.

S. Wakabayashi, et al., "Acute Toxicity and Mutagenicity Studies of Indigestible Dextrin, and Its Effect on Bowel Movement of the Rat", J. Food Hyg. Soc. Japan, 1992, 557–562.

M. Satouchi, et al., "Effects of Indigestible Dextrin on Bowel Movements", Jpn. J. Nutrition, 1993, 31–37.

Labell, F., "Functional Nutritional Fiber," Prepared Foods, 164(11):87 (1995).

Benefiber Product Label (1999).

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 4 and 45 are cancelled.

Claims 1, 6, 8-10, 12, 14, 23, 24, 35, and 36 are determined to be patentable as amended.

Claims 2, 3, 5, 7, 11, 13, 15-22, 25-34 and 37-44, dependent on an amended claim, are determined to be patentable.

New claims 46-52 are added and determined to be patentable.

1. A water composition for consumption by humans and animals comprising:
   between 0.1% and 10% by weight water-soluble indigestible fiber *selected from the group consisting of dextrins, maltodextrins, cellulose ethers, inulin, alginates, agar, carrageenan, gum tragacanth, gum karaya, gum ghatti, gum acacia, gum arabic, partially hydrolyzed products thereof and mixtures thereof*; and
   safe water,
   wherein fewer than 10 calories per 100 ml [is] *are* metabolized by a human when consuming the water composition and wherein the water composition contains less than 500 mg./l of soluble salts and essentially no organic acids.

6. A water composition for consumption by humans and animals comprising:
   between 0.1 % and 19% by weight water-soluble indigestible fiber selected from the group consisting of dextrins, maltodextrins, [galactomannans,] cellulose ethers, inulin, alginates, agar, carrageenan, [psyllium, guar gum,] gum [traganth] *tragacanth*, gum [karya] *karaya*, gum ghatti, gum acacia, gum arabic, partially hydrolyzed products thereof and mixtures thereof; and
   safe water,
   wherein the water and the water-soluble indigestible fiber form an optically clear solution, wherein fewer than 10 calories per 100 ml are metabolized by a human when consuming the water composition and wherein the water composition contains a nutritionally insignificant amount of soluble minerals and essentially no organic acids.

8. The water composition *of* claim 7, wherein the soluble food grade color acts as an indicator of an amount of the water soluble indigestible fiber contained in the water composition.

9. A water composition for consumption by humans and animals comprising:
   between 0.1% and 10% by weight water soluble indigestible fiber selected from the group consisting of dextrins, maltodextrins, inulin, [guar gum,] partially hydrolyzed products thereof and mixtures thereof; and
   safe water, wherein the water and the water soluble indigestible fiber form an optically clear solution,
   wherein fewer than 10 calories per 100 ml are metabolized by a human when consuming the water composition and wherein the water composition contains a nutritionally insignificant amount of soluble minerals and essentially no organic acids.

10. The water composition *of* claim 9 further comprising a soluble food grade color.

12. The water composition of claim 1, wherein said water-soluble fiber is selected [to satisfy] *so that the water composition satisfies* simultaneously both hydration requirements and fiber requirements when consumed.

14. The water composition *of* claim 1 formulated for managing constipation.

23. The water composition of claim 6, wherein the [water-like fluid] *water compostion* contains fewer than 500 mg./l of soluble salts.

24. The water composition of claim 6, wherein said water-soluble fiber is selected [to satisfy] *so that the water composition satisfies* both hydration requirements and fiber requirements when consumed.

35. A water composition for consumption by humans and animals comprising:
   between 0.1% and 10% by weight water-soluble indigestible fiber *selected from the group consisting of dextrins, maltodextrins, cellulose ethers, inulin, alginates, agar, carrageenan, gum tragacanth, gum karaya, gum ghatti, gum acacia, gum arabic, partially hydrolyzed products thereof and mixtures thereof*; and
   safe water,
   wherein fewer than 10 calories per 100 ml [is] *are* metabolized by a human when consuming the water composition and wherein the water composition contains a nutritionally insignificant amount of soluble minerals and essentially no organic acids.

36. The water composition of claim 35, wherein said water-soluble fiber is selected [to satisfy] *so that the water composition satisfies* simultaneously both hydration requirements and fiber requirements when consumed.

*46. The composition of claim 1, wherein the water soluble indigestible fiber is dextrin or a partially hydrolyzed product thereof.*

*47. The composition of claim 1, wherein the water soluble indigestible fiber is maltodextrin or a partially hydrolyzed product thereof.*

*48. The composition of claim 1, wherein the water soluble indigestible fiber is inulin or a partially hydrolyzed product thereof.*

*49. The composition of claim 1, wherein the water-soluble indigestible fiber is gum acacia or gum arabic or a partially hydrolyzed product thereof.*

*50. The composition of claim 9, wherein the water soluble indigestible fiber is dextrin or a partially hydrolyzed product thereof.*

*51. The composition of claim 9, wherein the water soluble indigestible fiber is maltodextrin or a partially hydrolyzed product thereof.*

*52. The composition of claim 9, wherein the water soluble indigestible fiber is inulin or a partially hydrolyzed product thereof.*

\* \* \* \* \*